US00PP19733P2

(12) United States Plant Patent
Hofmann

(10) Patent No.: US PP19,733 P2
(45) Date of Patent: Feb. 17, 2009

(54) ***CLEOME* PLANT NAMED 'INNCLEOSR'**

(50) Latin Name: *Cleome hybrida*
Varietal Denomination: Inncleosr

(75) Inventor: Silvia Hofmann, Mainz (DE)

(73) Assignee: Innovaplant GmbH & Co. KG, Gensingen (DE)

( * ) Notice: Subject to any disclaimer, the term of this patent is extended or adjusted under 35 U.S.C. 154(b) by 0 days.

(21) Appl. No.: 12/151,158

(22) Filed: May 2, 2008

(51) Int. Cl.
*A01H 5/00* (2006.01)

(52) U.S. Cl. ..... Plt./416
(58) Field of Classification Search ..... Plt./416
See application file for complete search history.

(56) References Cited

U.S. PATENT DOCUMENTS

PP15,969 P2 * 9/2005 Roberson ..... Plt./416

OTHER PUBLICATIONS

UPOV ROM GTITM Computer Database, GTI Jouve Retrieval Software 2008/02 Citations for 'Inncleosr'.*

* cited by examiner

*Primary Examiner*—Wendy C. Haas
(74) *Attorney, Agent, or Firm*—C. A. Whealy

(57) ABSTRACT

A new and distinct cultivar of *Cleome* plant named 'Inncleosr', characterized by its upright and compact plant habit; freely branching habit; freely flowering habit; long flowering period; purple-colored flowers; and good garden performance.

1 Drawing Sheet

Botanical designation: *Cleome hybrida.*
Cultivar denomination: 'Inncleosr'.

BACKGROUND OF THE INVENTION

The present invention relates to a new and distinct cultivar of *Cleome,* botanically known as *Cleome hybrida* and hereinafter referred to by the name 'Inncleosr'.

The new *Cleome* is a product of a planned breeding program conducted by the Inventor in Gensingen, Germany. The objective of the breeding program is to create new compact and freely-branching *Cleome* cultivars that flower for a long period of time and have attractive flower coloration.

The new *Cleome* originated from a cross-pollination made by the Inventor in 2002 in Gensingen, Germany of *Cleome hybrida* 'Linde Armstrong', not patented, as the female, or seed, parent with an unnamed proprietary seedling of *Cleome hybrida,* not patented, as the male, or pollen, parent. The new *Cleome* was discovered and selected by the Inventor as a single flowering plant within the progeny of the stated cross-pollination in a controlled greenhouse environment in Gensingen, Germany during the spring of 2003.

Asexual reproduction of the new *Cleome* by cuttings in a controlled environment in Gensingen, Germany since December, 2004, has shown that the unique features of this new *Cleome* are stable and reproduced true to type in successive generations.

SUMMARY OF THE INVENTION

The cultivar Inncleosr has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Inncleosr'. These characteristics in combination distinguish 'Inncleosr' as a new and distinct cultivar of *Cleome:*

1. Upright and compact plant habit.
2. Freely branching habit.
3. Freely flowering habit.
4. Long flowering period.
5. Purple-colored flowers.
6. Good garden performance.

Plants of the new *Cleome* differ from plants of the female parent, 'Linde Armstrong', in the following characteristics:

1. Plants of the new *Cleome* are not as compact as plants of 'Linde Armstrong'.
2. Plants of the new *Cleome* have larger flowers than plants of 'Linde Armstrong'.

Plants of the new *Cleome* differ from plants of the male parent selection in the following characteristics:

1. Plants of the new *Cleome* are more compact than plants of the male parent selection.
2. Plants of the new *Cleome* and the male parent selection differ in flower color as plants of the male parent selection have pink-colored flowers.

Plants of the new *Cleome* can be compared to plants of 'Robspivio', disclosed in U.S. Plant Pat. No. 15,969. In side-by-side comparisons conducted in Gensingen, Germany, plants of the new *Cleome* and 'Robspivio' differed in the following characteristics:

1. Plants of the new *Cleome* were more compact than plants of 'Robspivio'.
2. Plants of the new *Cleome* were more freely branching than plants of 'Robspivio'.
3. Plants of the new *Cleome* flowered for a longer period of time than plants of 'Robspivio'.

BRIEF DESCRIPTION OF THE PHOTOGRAPHS

The accompanying colored photographs illustrate the overall appearance of the new *Cleome,* showing the colors as true as it is reasonably possible to obtain in colored reproductions of this type. Colors in the photographs may differ slightly from the color values cited in the detailed botanical description which accurately describe the colors of the new *Cleome*.

The photograph at the bottom of the sheet comprises a side perspective view of a typical flowering plant of 'Inncleosr' grown in a container.

The photograph at the top of the sheet is a close-up view of a typical inflorescence of 'Inncleosr'.

DETAILED BOTANICAL DESCRIPTION

The aforementioned photographs and following observations, measurements and values describe plants grown in Bonsall, Calif. during the summer in one-gallon containers and under commercial practice in an outdoor nursery with day temperatures ranging from 18° C. to 38° C. and night temperatures ranging from 16° C. to 24° C. Plants were pinched and had been growing for two months when the photographs and description were taken. In the following description, color references are made to The Royal Horticultural Society Colour Chart, 1995 Edition, except where general terms of ordinary dictionary significance are used.

Botanical classification: *Cleome hybrida* 'Inncleosr'.

Parentage:

*Female, or seed, parent.*—*Cleome hybrida* 'Linde Armstrong', not patented.

*Male, or pollen, parent.*—Unnamed proprietary seedling of *Cleome hybrida,* not patented.

Propagation:

*Type.*—By cuttings.

*Time to initiate roots, summer.*—About one week at 25° C.

*Time to initiate roots, winter.*—About two weeks at 15° C.

*Time to produce a rooted young plant, summer.*—About 12 days at 25° C.

*Time to produce a rooted young plant, winter.*—About 20 days at 15° C.

*Root description.*—Fine, fibrous; white in color.

*Rooting habit.*—Freely branching; moderately dense.

Plant description:

*Plant form/habit.*—Herbaceous perennial. Upright and compact plant habit; inverted triangle. Freely branching habit; when pinched, about three primary lateral branches each with about three secondary laterals develop. Vigorous growth habit.

*Plant height.*—About 48 cm.

*Plant width* (*spread*).—About 39 cm.

*Lateral branches.*—Length: About 35 cm. Diameter: About 5 mm. Internode length: About 2.5 cm. Strength: Strong. Texture: Pubescent. Color: Close to 146A.

Foliage description:

*Arrangement.*—Alternate; compound, trifoliate.

*Leaf length.*—About 8.5 cm.

*Leaf width.*—About 10.5 cm.

*Leaflet length.*—About 6.5 cm to 7 cm.

*Leaflet width.*—About 2.5 cm.

*Leaflet shape.*—Elliptical.

*Leaflet apex.*—Broadly acute.

*Leaflet base.*—Cuneate.

*Leaflet margin.*—Entire.

*Leaflet texture, upper and lower surfaces.*—Sparsely pubescent.

*Venation pattern.*—Pinnate, arcuate.

*Color.*—Developing leaves, upper and lower surfaces: Close to 143A. Fully expanded leaves, upper surface: Close to 147A; venation, close to 147B. Fully expanded leaves, lower surface: Close to 147B; venation, close to 147B.

*Leaf petiole length.*—About 8.7 cm.

*Leaf petiole diameter.*—About 2 mm.

*Leaf petiole texture, upper and lower surfaces.*—Sparsely pubescent.

*Leaf petiole color, upper and lower surfaces.*—Close to 146A.

Flower description:

*Flower type/habit.*—Single zygomorphic flowers arranged in loose indeterminate terminal racemes; flowers face upright and outwardly. Freely flowering habit with about 24 to 28 open flowers and about 45 flower buds per raceme.

*Fragrance.*—None detected.

*Natural flowering season.*—Long flowering period. Plants flower continuously from April through October in California. Flowers not persistent.

*Postproduction longevity.*—Flowers last about three to four days on the plant.

*Flower buds.*—Height: About 1.7 cm. Diameter: About 3 mm. Shape: Lanceolate. Color: Close to 77B to 77C.

*Inflorescence height.*—About 10 cm to 12 cm.

*Inflorescence diameter.*—About 7 cm.

*Flower diameter.*—About 3.3 cm.

*Flower height.*—About 2.2 cm.

*Flower depth.*—About 2.5 cm.

*Petals.*—Quantity per flower: Typically four in a single whorl. Length: About 2 cm. Width: About 7 mm. Shape: Roughly spatulate. Apex: Broadly acute. Base: Attenuate. Margin: Entire. Texture, upper and lower surfaces: Smooth, glabrous; satiny. Color: When opening, upper surface: Close to 77B. When opening, lower surface: Close to 77C. Fully opened, upper surface: Towards the apex, close to 77B; midsection, close to 77C; towards the base, close to 75D. Color becoming closer to 78B with development. Fully opened, lower surface: Close to 77C to 77D. Color becoming closer to 82B with development.

*Sepals.*—Quantity per flower: Typically five in a single whorl. Length: About 6 mm. Width: About 1 mm. Shape: Lanceolate. Apex: Acuminate. Base: Truncate. Margin: Entire. Texture, upper and lower surfaces: Sparsely pubescent. Color, upper surface: Close to 146B. Color, lower surface: Close to 146A.

*Peduncles.*—Length: About 7 cm. Diameter: About 1.5 mm. Angle: Upright to about 30° from vertical. Strength: Strong; flexible. Texture: Sparsely pubescent. Color: Close to 148A.

*Pedicels.*—Length: About 2.1 cm. Diameter: Less than 1 mm. Angle: About 30° to 45° from vertical. Strength: Strong; flexible. Texture: Sparsely pubescent. Color: Close to 183C.

*Reproductive organs.*—Stamens: Quantity per flower: Typically five. Filament length: About 2 mm. Filament color: Close to 145C tinted with close to 183C to 183D. Anther shape: Lanceolate. Anther length: About 4 mm. Anther color: Close to 151A. Pollen amount: None observed. Pistils: Quantity per flower:

One. Pistil length: About 2 cm. Stigma shape: Rounded. Stigma color: Close to 183C. Style length: About 1.8 cm. Style color: Close to 183C. Ovary color: Close to 145C.

*Fruits/seeds.*—Fruit and seed development have not been observed on plants of the new *Cleome*.

Disease/pest resistance: Plants of the new *Cleome* have not been noted to be resistant to pathogens and pests common to *Cleome*.

Garden performance: Plants of the new *Cleome* have been observed to have good garden performance and tolerate rain, wind and temperatures ranging from about 5° C. to 38° C.

It is claimed:

1. A new and distinct *Cleome* plant named 'Inncleosr' as illustrated and described.

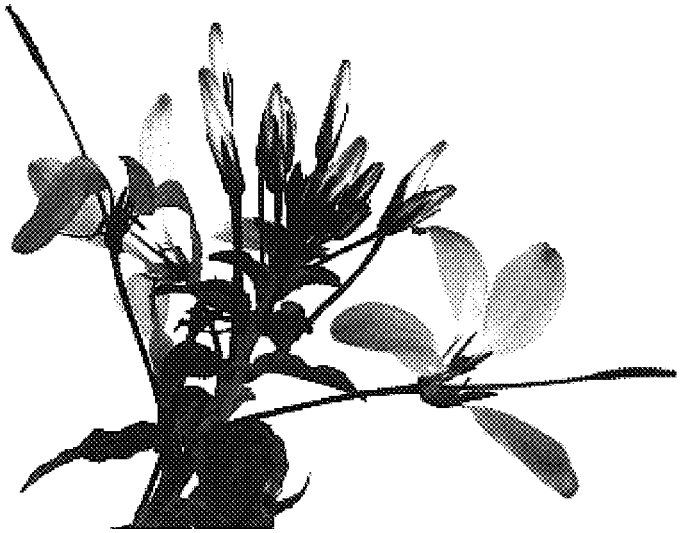
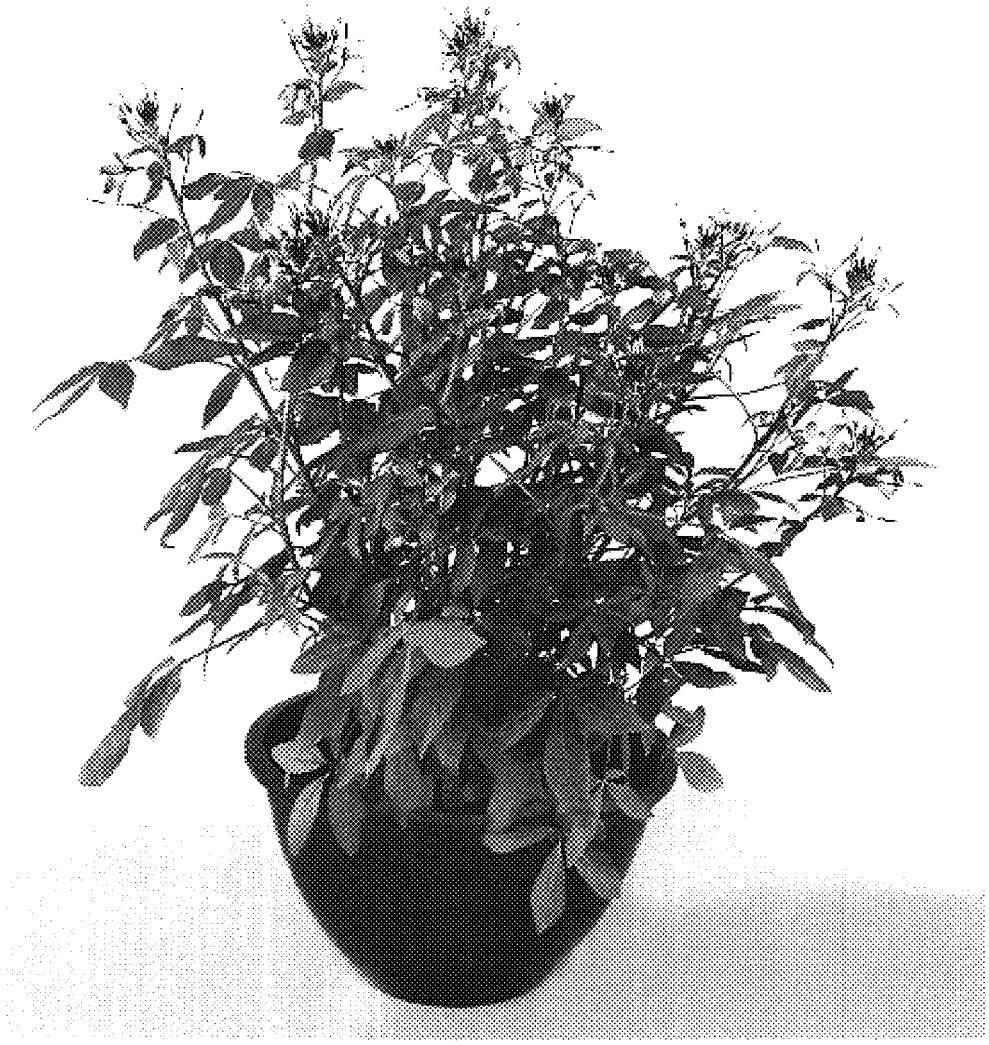

* * * * *